United States Patent [19]

Iffland et al.

[11] Patent Number: 5,945,560

[45] Date of Patent: Aug. 31, 1999

[54] CONTINUOUS PREPARATION OF ALKYL ESTERS OF (METH) ACRYLIC ACID

[75] Inventors: Gabriele Iffland, Marl; Albrecht Dams, Wachenheim; Alexander Weck, Bühlertal; Heinrich Aichinger, Mannheim; Holger Herbst, Frankenthal; Gerhard Nestler, Ludwigshafen; Herbert Exner, Waldsee, all of Germany

[73] Assignee: BASF Aktiengesellschaft, Ludwigshafen, Germany

[21] Appl. No.: 08/791,054

[22] Filed: Jan. 28, 1997

[30] Foreign Application Priority Data

Feb. 6, 1996 [DE] Germany .......................... 196 04 252

[51] Int. Cl.$^6$ .................................................. C07C 69/52
[52] U.S. Cl. ............................................................ 560/205
[58] Field of Search ............................................... 560/205

[56] References Cited

U.S. PATENT DOCUMENTS

| | | |
|---|---|---|
| 3,458,561 | 7/1969 | Theodor et al. . |
| 3,776,947 | 12/1973 | Shimizu et al. . |
| 3,882,167 | 5/1975 | Lohmar et al. . |
| 4,280,010 | 7/1981 | Erpenbach et al. . |
| 5,606,102 | 2/1997 | Fauconet et al. . |

FOREIGN PATENT DOCUMENTS

| | | |
|---|---|---|
| 0 694 524 | 1/1996 | European Pat. Off. . |
| 0 733 617 | 9/1996 | European Pat. Off. . |
| 0 765 859 | 4/1997 | European Pat. Off. . |
| 14 68 932 | 12/1966 | Germany . |
| 22 26 829 | 12/1973 | Germany . |
| 22 52 334 | 5/1974 | Germany . |
| 25 52 987 | 6/1977 | Germany . |
| 1 017 522 | 1/1966 | United Kingdom . |

*Primary Examiner*—Paul J. Killos
*Attorney, Agent, or Firm*—Oblon, Spivak, McClelland, Maier & Neustadt, P.C.

[57] ABSTRACT

In a process and an apparatus for the continuous preparation of alkyl esters of (meth)acrylic acid by reacting (meth) acrylic acid with alkanols having from 1 to 5 carbon atoms in a homogeneous, liquid, solvent-free phase at elevated temperature and in the presence of an acid esterification catalyst, in which the (meth)acrylic acid, the alkanol and the catalyst are fed to a reaction zone, the water formed is removed by rectification during a residence time as constituent of a mixture comprising alkanol in a rectification unit superposed on the reaction zone, the distillate thus obtained is separated into an organic phase comprising alkanol and an aqueous phase comprising water, the organic phase is returned to the rectification unit, the reaction mixture is discharged from the reaction zone and conveyed into a distillative separation zone comprising further rectification units and in the latter the alkyl (meth)acrylate formed is separated off.

18 Claims, 1 Drawing Sheet

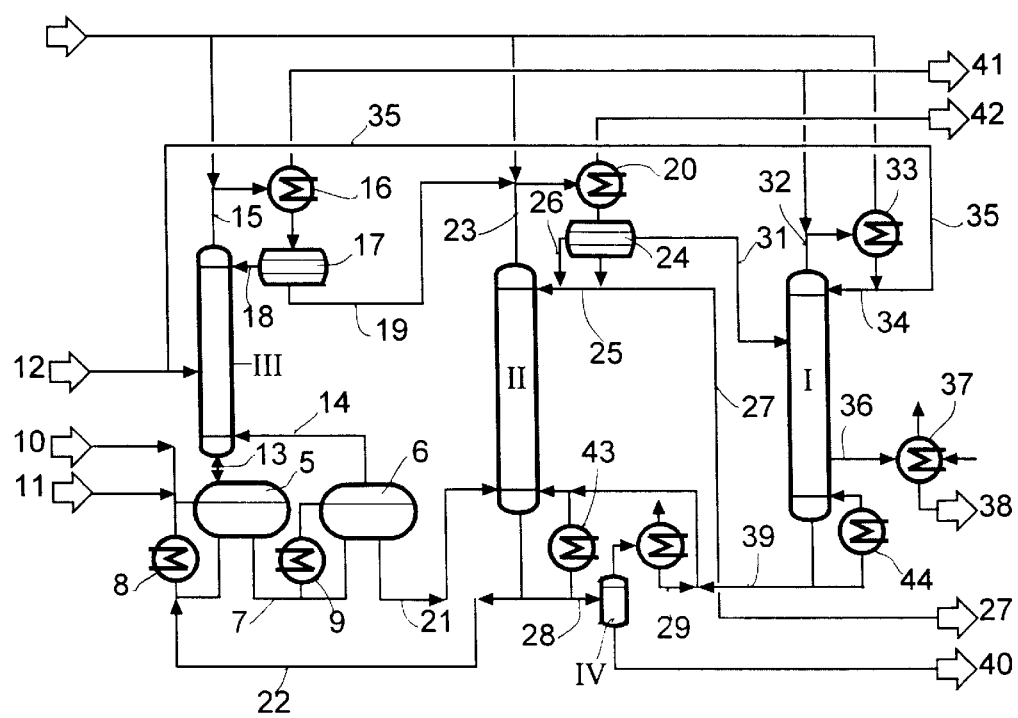

5,945,560

CONTINUOUS PREPARATION OF ALKYL ESTERS OF (METH) ACRYLIC ACID

The present invention relates to a process and an apparatus for the continuous preparation of alkyl esters of (meth)acrylic acid by reacting (meth)acrylic acid with alkanols having from 1 to 5 carbon atoms.

As is known, the term (meth)acrylic acid refers to acrylic acid or methacrylic acid. Alkyl esters of (meth)acrylic acid are generally known and are of importance, for example, as starting monomers for preparing aqueous polymer dispersions which are used, for example, as adhesives.

Processes for preparing alkyl (meth)acrylates by reacting (meth)acrylic acid with monohydric alkanols having from 1 to 5 carbon atoms in a homogeneous liquid phase at elevated temperature and in the presence of proton-donating catalysts are known and described, for example, in DE-A 14 68 932, 22 26 829 and 22 52 334. The reactions here are typical equilibrium reactions in which the degree of conversion of the (meth)acrylic acid and the respective alkanol into the corresponding ester is significantly restricted by the equilibrium constant. As a result, the unreacted starting materials have to be separated from the ester formed and returned to the reaction zone to achieve economic operation. The separation of the ester formed from unreacted (meth)acrylic acid is generally particularly difficult, since their boiling points are usually comparatively close to one another. For this reason, various measures for increasing the conversion of the (meth)acrylic acid into the corresponding esters have already been proposed, for example the use of an increased molar excess of alkanol over (meth)acrylic acid, the removal of the water of reaction by means of a suitable azeotrope-forming organic entrainer or the extraction of the ester formed during the reaction using a suitable solvent. However, these processes have the disadvantage that a great excess of alkanol has to be recovered or the entrainer or extractant has to be isolated. In addition, an increased excess of alkanol increases the formation of the dialkyl ether thereof as by-product.

GB-B 1 017 522 discloses a process for preparing n-butyl acrylate. As esterification conditions, it recommends a molar ratio of (starting) alkanol to (starting) acid of from 2.3 to 5, and a content of catalytically active sulfuric acid or organic sulfonic acid of from 0.5 to 5% by weight, based on the total mass of the reactants. Disadvantages of this procedure are the increased excess of alkanol required, which promotes the formation of undesired dialkyl ether, and also the yield of n-butyl acrylate, based on the amount of acrylic acid used, which is not completely satisfactory under the conditions prescribed.

DE-C 25 52 987 discloses a process for the continuous preparation of alkyl esters of acrylic acid by reacting acrylic acid and monohydric alkanols having from 1 to 4 carbon atoms in a homogeneous, liquid, solvent-free phase in a molar ratio of from 1(alkanol):1(acrylic acid) to 2(alkanol):1(acrylic acid) at elevated temperature and in the presence of sulfuric acid or organic sulfonic acid as catalyst, in which the acrylic acid, the alkanol and the catalyst are continuously fed to a reaction zone, the alkyl acrylate formed is removed by rectification during a residence time of some hours as constituent of at least one aqueous azeotrope comprising, apart from the alkyl acrylate, water or water and alkanol as further constituents via the top of a rectification column superposed on the reaction zone and having a pressure at the top of from 0.1 to 1 atm, the distillate obtained is separated into an organic phase comprising the acrylic ester formed and an aqueous phase, part of the organic phase is recirculated via the top of the rectification zone for the purpose of producing an increased separation action and, if desired, part of the aqueous phase is recirculated to maintain the composition of the aqueous azeotrope, the alkyl ester is separated in a manner known per se from the excess organic phase and part of the reaction mixture is discharged from the reaction zone, freed of high boilers by distillation and the distillate thus obtained is returned to the reaction zone.

The primary objective of DE-C 25 52 987 is the avoidance of undesired ether formation from the starting alkanol. However, a disadvantage of the procedure of DE-C 25 52 987 is that, despite distillative treatment of the discharge from the reaction mixture and return of the distillate thus obtained to the reaction zone, the yield of alkyl acrylate, based on the acrylic acid used, is not satisfactory. The reduction achieved in the dialkyl ether by-product formation is also not fully satisfactory. Furthermore, the residence time required according to the examples is not satisfactory. This also applies to the space-time yield. It is assumed that this is caused by the low concentration of catalyst.

It has therefore in the older (from priority), non-prepublished EP-A 0 733 617 already been proposed that the corresponding esterification process be carried out in the presence of increased concentrations of catalyst, which promotes the re-cleavage of oxy esters formed as further by-products in the esterification and thus increases the yield of ester based on (meth)acrylic acid used for a given residence time.

It has also already been proposed in the older (from priority), non-prepublished European Patent Application No. 96115454.9 that a further reduction in the amount of dialkyl ether be achieved, while obtaining a high yield of ester, by the reaction zone comprising a cascade of at least two, preferably continuously operated, reaction regions connected in series and the liquid discharge stream of one reaction region forming the feed stream to the next reaction region.

It is an object of the present invention to provide an esterification process for the preparation of alkyl esters of (meth)acrylic acid which makes possible not only an optimized yield, but also milder reaction conditions and thus greatly decreased ether formation, less formation of high boilers, a high space-time yield, increased flexibility of operation of the plant and also low capital costs owing to a minimized number of equipment items.

BRIEF DESCRIPTION OF THE DRAWING

Starting with the known process for the continuous preparation of alkyl esters of (meth)acrylic acid by reacting (meth)acrylic acid with alkanols having from 1 to 5 carbon atoms in a homogeneous, liquid, solvent-free phase at elevated temperature and in the presence of an acid esterification catalyst, in which the (meth)acrylic acid, the alkanol and the catalyst are fed to a reaction zone, the water formed is removed by rectification during a residence time as constituent of a mixture comprising alkanol in a rectification unit superposed on the reaction zone, the distillate thus obtained is separated into an organic phase comprising alkanol and an aqueous phase comprising water, the organic phase is returned to the rectification unit, the reaction mixture is discharged from the reaction zone and conveyed into a distillative separation zone comprising further rectification units and in the latter the alkyl (meth)acrylate formed is separated off, the inventive process is characterized in that a) (meth)acrylic acid and an alkanol having from 1 to 5 carbon atoms are reacted in a molar ratio of from 1:0.75 to 1:2, b) the organic phase formed in the rectification unit is essentially completely returned to the rectification unit, c) the aqueous phase formed in the rectification unit is essentially removed from the system, d) the reaction mixture discharged from the reaction zone is, with addition of water, fed to a further rectification unit and in this is separated into a product comprising the catalyst and the remaining (meth)acrylic acid and a product comprising the alkyl ester of (meth)acrylic acid, remaining alkanol and water, e) the product formed in the rectification unit is essentially completely returned to the reaction zone, f) the product from the rectification unit is separated into an organic phase comprising the alkyl ester of (meth) acrylic acid and an aqueous phase and g) the organic phase formed in the rectification unit is fed to a further rectification unit and in this the alkyl ester of (meth)acrylic acid is separated from the remaining alkanol and the remaining alkanol is returned to the reaction zone.

The bottom product formed in the rectification unit II can advantageously be returned essentially completely to the rectification unit I.

Both here and below, the term rectification unit is used as a general designation for apparatuses in which heat input generates vapors which rise and are in contact with liquid phase flowing downward. These also include simple distillation columns. In general, however, they are rectification columns having internal fittings to provide efficient contact between liquid and vapor. Such internal fittings are trays such as bubble cap trays, perforated trays, in particular dual flow trays, beds, packings or the like. To simplify the understanding of the relationships, the various rectification units are designated by Roman numerals. The various, specifically described products are also designated in this way.

Owing to the relatively low volatility of the acid esterification catalyst and also because the water is removed from the reaction zone via the rectification unit III, the proportion by weight of catalyst in the reaction mixture both in the esterification and in the rectification unit I increases within the reaction zone from the first reaction zone to the second rectification zone and, if a plurality of reaction regions are resent, also from reaction region to reaction region.

The esterification is carried out at reduced pressure to remove the water of reaction and is separated from the subsequent separation of the alkyl (meth)acrylate both in space and by means of regulating devices. Esterification and subsequent separation of the alkyl (meth)acrylate in the rectification zone can therefore be adjusted very flexibly. Water, which is introduced into the second rectification zone for the azeotropic removal of the alkyl (meth)acrylate, therefore has only a slight effect on the esterification.

The reaction zone consists of one or more reaction regions. In the embodiment of the invention having a plurality of reaction regions, it is advantageous to cascade these. The liquid discharge stream of one reaction region here forms the feed to the downstream reaction region. This can occur by means of an overflow. If the individual reaction regions are apparatuses separated from one another, there are, taking capital costs into consideration, from 2 to 4 of these. If more than one reaction region is created within one and the same reactor (eg. by the use of separating plates), the number of reaction regions can also be greater than 4. In the case of a plurality of reaction regions, the vapors are fed to the reaction regions of a common rectification column whose liquid outflow advantageously goes into the first reaction region. The distillate is, after condensation, divided into two phases, an organic phase consisting largely of alkanol and an aqueous phase consisting largely of water, and the organic phase is returned essentially completely, preferably completely, to the rectification unit III.

The temperature of the reaction mixture in the various reaction regions normally corresponds to the boiling point of the respective reaction mixture at the pressure set, preferably from 0.1 to 1 atm, particularly preferably from 0.1 to 0.5 atm, ie. it normally increases along the cascade (in the case of a plurality of reaction regions) to the bottom of the rectification unit I.

The separation of esterification reaction and distillative removal of the alkyl ester of (meth)acrylic acid allows milder reaction conditions. The reaction can be carried out in all reaction regions at a pressure from 100 mbar to atmospheric pressure, preferably at a pressure at the top (of the water separation column) of from 200 to 700 mbar, particularly preferably from 300 to 450 mbar, and at from 90° C. to 115° C. The pressure can be the same in all reaction regions. The rectification unit I is preferably operated at atmospheric pressure and at from 100° C. to 130° C. The temperature in the rectification unit I downstream of the reaction zone should not exceed 135° C., in order to suppress undesired polymerizations as secondary reactions.

According to an advantageous embodiment of the invention, the content of catalytically active acid in the first reaction region, based on the reaction mixture present therein, is from 0.1 to 10% by weight, preferably from 0.1 and 6% by weight, of para-toluenesulfonic acid or an amount equimolar thereto of another organic sulfonic acid and/or sulfuric acid. The corresponding acid content in the liquid phase of the rectification unit I, based on the mixture present therein is preferably from 2.5 to 25% by weight. The total residence time of the reactants in the reaction zone is generally from 0.25 to 15 hours, preferably from 1 to 7 hours, particularly preferably from 2 to 5 hours. It preferably decreases from region to region in a downstream direction. In the liquid phase of the rectification unit I, it is preferably from 0.2 to 5 hours. In the rectification unit I, partial dissociation of the oxy esters formed to a slight extent in the esterification (mainly alkoxy esters and (meth)acryloxy esters of (meth)acrylic acid) occurs owing to the increased catalyst content. This is an important advantage of the process of the present invention.

One embodiment of the process of the present invention comprises recirculating part of the liquid continuously from the first rectification unit I downstream of the reaction zone to the reaction zone, preferably to the first reaction region. A further part of the bottom liquid of this rectification unit I is, to eliminate high boilers, fed, preferably continuously, to a further distillation unit in which the low boilers are separated from the high boilers (oligomers and polymers formed), preferably in one stage and batchwise. These low boilers are essentially alkyl (meth)acrylate, water, alkanol and (meth)acrylic acid. They are fed to the rectification unit I to increase the yield. In the additional distillation unit, part of the oxy esters is likewise dissociated, so that the losses of useful materials can be kept very low.

From the rectification unit I, a partial amount corresponding to from 20% by weight to 95% by weight, preferably from 35 to 55% by weight, of the amount fed to this rectification unit I from the last reaction region is advantageously returned to the reaction zone. To limit the proportion of high-boiling by-products which cannot be dissociated, it is sufficient to bleed off from the rectification unit I an amount of from 1 to 20% by weight, preferably from 2 to 10% by weight, based on the feed of starting materials to the reaction zone, to a further distillation (rectification) unit IV. The amount of high boilers removed from this distillation (rectification) unit IV is from 3 to 30% by weight, generally 5–15% by weight, based on the amount fed to this zone. The total losses based on alkyl acrylate formed are less than 1.5%.

An amount of fresh catalyst corresponding to the amount of catalyst present in the high boilers removed from the distillation (rectification) unit IV is fed into the first reaction region, preferably continuously. This leads to the required concentration of catalyst being maintained at a constant level in the reaction zone and in the rectification unit I. The circulation of catalyst makes a catalyst work-up step superfluous and the consumption of fresh catalyst is reduced. Process stabilizer is also removed from the system in the bleed stream, so that the stabilizer content settles down to a steady-state value.

The conversions based on the amount of (meth)acrylic acid used are typically $\geq 95$ mol %. Advantageously, the first reaction region is operated at a conversion of $\geq 90$ mol %. If a plurality of reaction regions connected in series (cascade) is used, these are advantageously configured in such a way that the residence time decreases along the cascade from reaction region to reaction region.

According to an advantageous embodiment of the invention, the molar ratio of (meth)acrylic acid feed to alkanol feed is from 1:0.75 to 1:2. Of very particular advantage is a stoichiometric ratio of 1:1. Stoichiometric use of the starting materials has the advantage that, besides the low temperature in the esterification, a very great reduction in dialkyl ether formation is achieved. Furthermore, this results in an excess of (meth)acrylic acid existing in the liquid phase of the rectification unit I at elevated catalyst concentrations, which in turn has the advantage that the alkanol formed from the simultaneous in situ dissociation is reacted to give alkyl (meth)acrylate instead of reacting further to form dialkyl ether.

It is particularly advantageous to use para-toluenesulfonic acid and/or other organic sulfonic acids and/or sulfuric acid as esterification catalysts. The content of catalytically active acid in the reaction zone, based on the reaction mixture present therein, can be from 0.1 to 6% by weight of para-toluenesulfonic acid and/or an amount equimolar thereto of further organic sulfonic acids and/or sulfuric acid. The content of catalytically active acid in the liquid phase of the rectification unit I, based on the reaction mixture present therein, can be from 2.5 to 25% by weight of para-toluenesulfonic acid and/or an amount equimolar thereto of another organic sulfonic acid and/or sulfuric acid.

Since the acrylic acid used contains small amounts of acetic acid, alkyl esters of acetic acid are formed as by-products in addition to dialkyl ether. Both secondary components go over at the top of the rectification unit III superposed on the reaction zone and, in the distillative removal of water, remain in the alkanol, ie. the organic phase of the rectification unit III and are advantageously returned to the reaction zone. As a result, both impurities accumulate in the organic phase. It is particularly advantageous to use a crude acrylic acid depleted in acetic acid. In this case it is sufficient, owing to the very small amounts of dialkyl ether and alkyl acetate, to bleed off a substream of the organic phase, generally less than 1% of the amount of alkanol used. In this way, low boilers are removed from the system and do not get into the pure product.

In a further embodiment, a substream of the organic phase of the top product of the rectification column III superposed on the reaction zone is separated in a further column into a top product comprising dialkyl ether, alkyl acetate, alkanol and water, and a bottom product consisting largely of alkanol. The alkanol from the bottom of this rectification column is returned in the manner described above to the reaction zone, preferably via the rectification column III, to separate off the low boilers.

The organic phase of the top product of the rectification unit I comprises the alkyl (meth)acrylate as main component as well as alkanol and water. In this rectification column, (meth)acrylic acid and alkoxyalkyl esters of (meth)acrylic acid (hereinafter also abbreviated as alkoxy esters) are prevented by means of appropriate setting of the operating parameters from going into the top product and require no further separation.

The downstream rectification unit II (alkanol/ester separation) is preferably operated in such a way that alkanol containing small amounts of water and alkyl acrylate is taken off as top product at the upper end of this rectification column II and is conveyed back to the reaction zone, and pure alkyl (meth)acrylate is taken off at the lower end of the rectification column. A particularly preferred embodiment of the alkanol/ester separation comprises taking off the pure ester in vapor form as a side stream at the lower end of the rectification column II above the vaporizer, between the vaporizer and the fifth tray, most appropriately above the vaporizer. This gas stream is condensed and restabilized in a known manner using a storage stabilizer (eg. hydroquinone monomethyl ether). To avoid the formation of high boilers, a substream is taken from the vaporizer of the rectification column II which serves to separate the alkanol and ester, generally a substream of from 1 to 20%, preferably from 1 to 5%, of the amount of feed to this column, and is returned to the reaction zone or preferably to the rectification unit I. Further purification of the pure ester taken off in vapor form is not necessary.

A favorable embodiment comprises recirculating the top product of the rectification column II for the alkanol/ester separation to the upper part of the rectification column III superposed on the reaction zone, in order to prevent water present therein from getting into the reaction mixture.

In a further embodiment, the alkyl (meth)acrylate is taken off in liquid form at the bottom of the alkanol/ester separation column (rectification column II) and the desired pure (meth)acrylic ester is separated off via the top in a downstream high-boiler rectification column. The bottom liquid from the high-boiler rectification column, which contains the by-products having relatively high boiling points, is advantageously returned to the reaction zone and/or to the rectification unit I, preferably directly.

The process of the present invention is particularly preferably employed for preparing n-butyl acrylate.

The vapors formed in the rectification unit I, which is according to the present invention separated physically from the reaction zone, are, as described above, fed to a rectification zone. With regard to the mixture separated off via the top of this zone and containing the target ester, essentially two situations can be distinguished. If the mixture separated off is a heteroazeotrope, as in the case of the preparation of n-butyl acrylate, the azeotrope separates of its own accord after condensation into an aqueous phase and an organic phase. The aqueous phase normally consists mainly of water and some alkanol, the organic phase generally consists essentially of the ester formed and alkanol. To adjust the rectificative separation action, an appropriate part of the organic phase is returned via the top to the rectification zone.

To maintain the composition of the aqueous azeotrope, an appropriate part of the aqueous phase is returned to the rectification zone I, preferably likewise via the top of the superposed rectification column. Alkanol present in the part of the aqueous phase which is not recirculated can be separated off, for example by stripping (eg. using air or steam) and returned to the reaction zone. It is advantageously returned directly. The essentially pure water formed here is discharged.

If the aqueous azeotrope containing the target ester and separated off continuously via the top of a rectification zone of a process according to the present invention is not a heteroazeotrope, then this does not separate of its own accord after condensation into an aqueous phase and an organic phase. However, this separation can easily be achieved by extracting the alkanol present in the azeotrope by means of water and fractionating the resulting water/alkanol mixture by rectification. The alkanol is advantageously returned to the reaction zone, preferably via the top of the superposed rectification zone.

If a heteroazeotrope is formed, a particularly preferred embodiment comprises conveying the excess aqueous phase (reaction water from the esterification) obtained from the rectification column m superposed at the top of the reaction zone to the top product of the rectification zone I. The aqueous phase of this heteroazeotrope takes up less alkanol after separation of the phases owing to the high alkyl (meth)acrylate content and of the lower alkanol content of the organic phase. The excess water of reaction, which contains from 1% by weight to 5% by weight, on average 2.5% by weight, of alkanol, can be removed from this aqueous phase obtained at the top of the rectification unit I. In general, a further process step comprising stripping of the alkanol can be omitted.

The azeotrope taken off from the rectification unit I generally contains no starting acid if the rectificative separation action has been adjusted correctly. However, should the latter not be the case, the starting acid can be separated off by extraction with water or an alkaline solution and the extract can, if appropriate, subsequently be worked up in a manner known per se.

In the process of the present invention, both the esterification reaction and the thermal separation are preferably carried out in the presence of customary amounts of polymerization inhibitors customary per se. From 0.01 to 0.1% by weight of a suitable polymerization inhibitor, based on the amount of the a,o-monoethylenically unsaturated monomers, is generally used. It is advantageously added at the top of the rectification column III superposed on the reaction zone, at the top of the rectification unit I and at the top of the rectification unit II (alkanol/ester separation column). Suitable polymerization inhibitors are, for example, phenolic compounds such as hydroquinone, hydroquinone monomethyl ether, but also p-benzoquinone, phenothiazine, methylene blue, phenylenediamine and/or air.

In comparison with the processes of the prior art, the process of the present invention has a distinctly reduced number of substeps and separation operations, gives high flexibility owing to the separation of water removal from the esterification and removal of the alkyl (meth)acrylate by addition of water, has reduced residence times, gives an increased yield of the ester desired based on starting acid used, produces a reduced amount of ether, results in low high-boiler by-product formation and thus a reduced discharge of the liquid phase from the reaction and rectification units and is also notable for the fact that re-cleavage of high-boiler bleeds and recovery of useful materials occurs in a simple vaporizer/condenser system (fourth rectification unit) without a further separation column. The resulting reduced losses because of high-boiler removal are attributable to a partial re-cleavage of relatively high-boiling oxy esters (eg. alkoxypropionic esters) in the rectification units I and IV.

In one favorable embodiment, the entire process is carried out using a total of only three separation columns (units):

1. a rectification unit III for removing water from the reaction,
2. a rectification unit I for separating the alkyl (meth)acrylate from high-boilers, acrylic acid and catalyst, and
3. a rectification unit II for returning the alkanol and isolating the pure ester via a side offtake.

Another embodiment requires two additional separation columns for removing acetate from the organic phase of the top product of the rectification unit III superposed on the reaction zone and for stripping alkanol from the water of reaction. However, owing to the small amounts to be separated off, the separation columns (units) require only a small capital investment and in no way adversely affect the other advantages of the process.

Further details and advantages of the invention may be found in the following examples described with the aid of the drawing, wherein this drawing shows in FIG. 1 a schematic plan of an apparatus for preparing n-butyl acrylate.

DESCRIPTION OF THE DRAWING

The rectification columns (units) are provided with Roman reference numerals. In addition, in the interests of clarity, the product designations, generally provided with Roman numerals and additionally are precised in the specific examples.

The plant shown in the drawing for carrying out the process of the present invention for preparing n-butyl acrylate has three rectification columns I, II, III and a distillation unit IV; butanol is n-butanol. In addition, it is provided with two esterification reactors 5 and 6 which are connected in series by means of a line 7 and thus form a reaction cascade. Convection vaporizers 8 and 9 are connected to the reactors 5 and 6. 4 mol/h of acrylic acid were fed via line 10 into the first reactor 5 and 4 mol/h of butanol were fed in through line 12 via the column III superposed on the first reactor 5. In addition, aqueous acid as catalyst was introduced via line 11 into the first reactor 5 in an amount of 1.5% by weight based on the starting materials used. The reaction in the first reactor 5 was carried out at 100° C., in the downstream second reactor 6 at 105° C., at a system pressure of 380 mbar and a residence time of about 3 hours in the reaction zone.

The vapors rising from the reactors 5 and 6 were introduced via lines 13 and 14 into a bubble cap tray column III as first rectification unit and rectified therein. The top product of this column III was free of acrylic acid. It was condensed in a surface condenser 16 and conveyed to a separator 17. There, an organic phase containing 70% by weight of butanol, 12% by weight of butyl acrylate, ≦13% by weight of water, 4% by weight of butyl acetate and 2000 ppm of dibutyl ether separated out. It was all returned through line 18 as runback to the column III. The aqueous phase formed in the separation, which still contained 6% by weight of butanol, 300 ppm of butyl acrylate and 750 ppm of butyl acetate, was separated off completely to shift the reaction equilibrium and fed via line 19 to the decanter 24 of the downstream rectification column I.

The liquid raw ester flowing from the second reactor 6 was fed via line 21 to the rectification column I. It contained 78% by weight of the desired product n-butyl acrylate, about 4% by weight of each of the unreacted starting materials butanol and acrylic acid, about 5% by weight of catalyst as well as 0.2% by weight of water and at most 20 ppm of dibutyl ether. The remainder was high-boiling by-products, in particular oxy ester compounds.

Acrylic acid and high boilers together with part of the product and the alcohol were separated off as bottom product (product II) in the rectification column I fitted with 25 mesh trays and operated at ambient pressure. The bottom product (product II) contained 20% by weight of acrylic acid, 45% by weight of butyl acrylate, 3% by weight of butanol, 8% by weight of water. A partial amount of about 45% by weight of the feed amount fed in through line 21 was returned via line 22 to the first reaction region.

The major part of the high boilers (up to 80% of the amount fed in) was cracked in the liquid phase of the rectification column I to form starting materials and products. Owing to the high acrylic acid and water content of the bottom product, only insignificant amounts of low-boiling by-products were formed ($\leq 200$ ppm of dibutyl ether). These by-products together with the main product stream were separated off as a low-boiling minimum heteroazeotrope via the top of the column I and conveyed via line 23 to the condenser 20. Here, the liquid in the column and also the top product separated into an aqueous phase and an organic phase. To maintain the heteroazeotrope in the column I, aqueous phase from the top condenser 24 was fed into the column through line 25 and organic phase was fed in as runback through line 26. The aqueous phase contained $\leq 3\%$ by weight of organic constituents, primarily butanol.

The organic phase contained from 75 to 85% by weight of butyl acrylate, from 14 to 20% by weight of butanol, from 2 to 3% by weight of water, 1500 ppm of butyl acetate. The excess water corresponding to the conversion in the reaction was removed from the system through line 27. 5% by weight of the bottom product (product II), based on the amount of starting materials fed to the esterification, was discharged via line 28 and fed to a stirred vessel IV. There, the product was evaporated batchwise at ambient pressure and 180° C. until the viscosity rose distinctly. The starting materials butanol and acrylic acid still present therein and the product butyl acrylate were first distilled off. The amount of distillate was up to about 65% by weight, based on the amount fed in. In the subsequent cracking of the high boilers, the bottom discharge was evaporated to about 15% of its original mass, and low-boiling by-products such as butenes and dibutyl ether were formed to a small extent only toward the end. The condensed vapors from the cracking in the stirred vessel IV consisted essentially of acrylic acid, butyl acrylate, butanol and water. This liquid was fed directly to the bottom of the column I for the high-boiler separation. A further rectification was not carried out.

The organic top product (product I) from the azeotropic distillation in the column I, which was free of high boilers and acrylic acid, was fed via line 31 to a distillation column II provided with 25 trays and rectified therein. Butanol, residual water and any low boilers present therein were here taken off as top product via line 32 (product V). This contained from 65 to 70% by weight of butanol, from 20 to 30% by weight of butyl acrylate, from 8 to 10% by weight of water, $\leq 500$ ppm of dibutyl ether, <4000 ppm of butyl acetate. This top product (product V) was condensed in a condenser 33 and a partial amount was returned through line 34 as runback to the top of the rectification column II. The main amount was fed through line 35, together with the fresh alcohol fed in through line 12, to the esterification via the first column I. The butyl acrylate was concentrated in the liquid phase of this column II and, to achieve the desired color number and to separate off the process stabilizer, is taken off in vapor form as a side stream through line 36, condensed in the condenser 37 and conveyed away through line 38. The pure product contained $\leq 50$ ppm of butanol, $\leq 50$ ppm of dibutyl ether, $\leq 150$ ppm of water, $\leq 50$ ppm of acrylic acid.

A small bottom bleed stream (product VI) comprising $\leq 2\%$ by weight of the feed to the column was conveyed via line 39 to the bottom of the high-boiler separation in column I.

The residue was discharged from the stirred vessel IV through line 40. Line 41 connected to columns III and H to a vacuum pump. Waste air from the column was conveyed away through line 42. The liquid phase of the columns I and II was heated by means of convection vaporizers 43 and 44 respectively.

The pure ester had a purity of $\geq 99.9\%$, the yield based on acrylic acid and butanol was in each case 98% of theory.

In a further experiment, the second esterification reactor 6 was taken out of operation and the raw ester from the first reactor 5 was introduced via line 7 directly into the bottom of the column I. The reaction was carried out at 105° C. With the same feed flows and therefore a reduced residence time compared with the variant with two reactors, and otherwise identical process parameters, it was possible to obtain a raw ester containing 71% by weight of the desired product n-butyl acrylate, 0.4% by weight of water, at most 20 ppm of dibutyl ether, a starting material content (butanol and acrylic acid) of about 7% by weight for each and also up to 5% by weight of catalyst. The remainder was high-boiling by-products, in particular oxy ester compounds.

The raw ester thus produced was purified by a method similar to the first experiment under identical process parameters in the work-up part to give a 99.9% pure product at a total yield of 98% based on the starting materials.

We claim:

1. A process for the continuous preparation of alkyl esters of (meth)acrylic acid by reacting (meth)acrylic acid with alkanols having from 1 to 5 carbon atoms in a homogeneous, liquid, solvent-free phase at elevated temperature and in the presence of an acid esterification catalyst, in which the (meth)acrylic acid, the alkanol and the catalyst are fed to a reaction zone, the water formed is removed by rectification during a residence time as constituent of a mixture comprising alkanol in a rectification unit (III) superposed on the reaction zone, the distillate thus obtained is separated into an organic phase comprising alkanol and an aqueous phase comprising water, the organic phase is returned to the rectification unit (II), the reaction mixture is discharged from the reaction zone and conveyed into a distillative separation zone comprising further rectification units and in the latter the alkyl (meth)acrylate formed is separated off, wherein a) (meth)acrylic acid and an alkanol having from 1 to 5 carbon atoms are reacted in a molar ratio of from 1:0.75 to 1:2, b) the organic phase formed in the rectification unit (III) is essentially completely returned to the rectification unit, c) the aqueous phase formed in the rectification unit (III) is essentially removed from the system, d) the reaction mixture discharged from the reaction zone is, with addition of water, fed to a further rectification unit (I) and in this is separated into a product (II) comprising the catalyst and the remaining (meth)

acrylic acid and a product (I) comprising the alkyl ester of (meth)acrylic acid, remaining alkanol and water, e) the product (II) formed in the rectification unit (I) is essentially completely returned to the reaction zone, f) the product (I) from the rectification unit (I) is separated into an organic phase comprising the alkyl ester of (meth)acrylic acid and an aqueous phase and g) the organic phase formed in the rectification unit (I) is fed to a further rectification unit (II) and in this the alkyl ester of (meth)acrylic acid is separated from the remaining alkanol and the remaining alkanol is returned to the reaction zone.

2. A process as claimed in claim 1, wherein the reaction zone comprises a cascade of at least two reaction regions connected in series, and the discharge stream of one reaction region forms a feed stream to a downstream reaction region, and wherein the temperature in the first reaction region is 70–105° C., and in the last region is 100–160° C., and wherein the reaction temperature rises along the cascade.

3. A process as claimed in claim 2, wherein the pressure in all reaction regions is from 100 mbar to atmospheric pressure, wherein the total residence time for the reactants in the reaction regions is from 0.25 to 15 hours, and wherein the residence time decreases in successive reaction regions.

4. A process as claimed in claim 1, wherein the rising vapors from the reaction regions are fed to a rectification unit (III) whose liquid runback is returned only to the first reaction region.

5. A process as claimed in claim 1, wherein the catalyst used comprises para-toluenesulfonic acid and/or an other organic sulfonic acid such as methanesulfonic acid, benzenesulfonic acid, dodecylbenzenesulfonic acid and/or sulfuric acid, wherein the content of catalytically active acid in the reaction zone, based on the reaction mixture present therein, is from 0.1 to 10% by weight, of para-toluenesulfonic acid and/or an amount equimolar thereto of another organic sulfonic acid and/or sulfuiric acid, wherein the content of catalytically active acid in the liquid phase of the rectification unit (I), based on the mixture present therein, is from 2.5 to 25% by weight of para-toluenesulfonic acid and/or an amount equimolar thereto of another organic sulfonic acid and/or sulfuric acid.

6. A process as claimed in claim 1, wherein both the (meth)acrylic acid and the catalyst are fed directly to the reaction zone, the alkanol to be esterfied, is n-butanol and is fed to the reaction zone via the rectification unit (III), wherein the rectification unit (III) is a rectification column, the reaction regions comprise reactors having convection vaporizers, and wherein the aqueous phase obtained at the top of the rectification unit (III) is completely discharged.

7. A process as claimed in claim 6, wherein the product (I) is separated into an organic phase comprising the n-butyl ester of (meth)acrylic acid and n-butanol and an aqueous phase, part of the aqueous phase is returned to the rectification unit (I), a liquid aqueous phase and a liquid organic phase are present in the rectification unit (I), the rectification unit (I) is a rectification column (I), the product mixture discharged from the reaction zone is fed to the lower part of the rectification column (I) and the water addition occurs in the upper part of the rectification column (I), and wherein part of the resulting organic phase comprising the n-butyl ester of (meth)acrylic acid and n-butanol is returned to the upper part of the rectification column (I).

8. A process as claimed in claim 6, wherein the product (II) formed in the rectification unit (I) and comprising the catalyst and the remaining (meth)acrylic acid is returned essentially completely to the reaction zone, preferably to the first reaction region, either directly and/or via the rectification unit (III), wherein part of the product (II) formed in the rectification unit (I) is discharged and fed to a distillation unit (IV) and in this is separated into a product (III) comprising n-butanol, (meth)acrylic acid and the n-butyl ester of (meth)acrylic acid and a product (IV) comprising the acid esterification catalyst and components having higher boiling points than the n-butyl ester of (meth)acrylic acid, and wherein the product (III) is returned to the rectification unit (I) and/or the reaction zone.

9. A process as claimed in claim 6, wherein the organic phase of the product (I) is fed to a rectification unit (II) and in this is separated into a) a product (V) comprising remaining n-butanol and components having lower boiling points than n-butyl (meth)acrylate, b) n-butyl (meth)acrylate and c) a product (VI) having a boiling point higher than n-butyl (meth)acrylate, the product (V) is returned to the reaction zone, via the rectification unit (III), the product (VI) is returned to the rectification unit (I), the rectification unit (II) is a rectification column (II), and wherein the product (V) is taken off in the upper part of the rectification column (II), the product (VI) is taken off from the bottom of the rectification column (II) and the n-butyl (meth)acrylate is taken off in vapor form while rising as a lateral branch stream in the lower part of the rectification column (II).

10. The process of claim 2, wherein said cascade has from 2 to 4 reaction regions.

11. The process of claim 2, wherein said reaction regions are separated from one another in space.

12. The process of claim 11, wherein the said cascade has from 2 to 4 reaction regions.

13. The process of claim 1, wherein the temperature in the first reaction region is from 80–130° C. and in the last reaction region is from 105–130° C.

14. The process of claim 3, wherein the pressure in all reaction regions is from 200 mbar to 700 mbar.

15. The process of claim 5, wherein said catalytically active acid is present in an amount of from 0.1 to 6% by weight, based on the reaction mixture present.

16. The process of claim 14, wherein the total residence time of the reactants in the reaction regions is from 1 to 7 hours.

17. The process of claim 15, wherein the total residence time of the reactants in the reaction regions is from 2 to 5 hours.

18. The process of claim 14, wherein the pressure in all reaction regions is the same.

* * * * *